(12) United States Patent
Seol

(10) Patent No.: US 8,419,599 B2
(45) Date of Patent: Apr. 16, 2013

(54) UNDERWATER EXERCISE AND PHYSICAL THERAPY DEVICE FOR JOINT RELEASE AND SPINAL ADJUSTMENT

(76) Inventor: Gye-Hyun Seol, Geoje-si (KR)

( * ) Notice: Subject to any disclaimer, the term of this patent is extended or adjusted under 35 U.S.C. 154(b) by 350 days.

(21) Appl. No.: 12/735,419

(22) PCT Filed: Mar. 20, 2009

(86) PCT No.: PCT/KR2009/001448
§ 371 (c)(1),
(2), (4) Date: Jul. 14, 2010

(87) PCT Pub. No.: WO2010/071264
PCT Pub. Date: Jun. 24, 2010

(65) Prior Publication Data
US 2011/0060364 A1 Mar. 10, 2011

(30) Foreign Application Priority Data
Dec. 16, 2008 (KR) .................. 10-2008-0127910

(51) Int. Cl.
*A63B 21/055* (2006.01)
*A63B 21/065* (2006.01)
*A63B 23/02* (2006.01)
*A63B 69/12* (2006.01)

(52) U.S. Cl.
USPC ............ 482/105; 482/55; 482/69; 482/124; 482/143; 602/32; 602/36; 441/129

(58) Field of Classification Search ............ 482/55, 482/67, 105, 69, 78, 79, 121, 122, 124, 143; 602/32, 36, 13, 19, 23; 606/241; 441/129, 441/131, 108, 110, 113, 121; 177/207; 601/33, 601/34, 35
See application file for complete search history.

(56) References Cited

U.S. PATENT DOCUMENTS

| | | | | | |
|---|---|---|---|---|---|
| 156,443 | A | * | 11/1874 | Stoner ........................... | 441/110 |
| 636,893 | A | * | 11/1899 | Burton .......................... | 441/110 |
| 1,006,909 | A | * | 10/1911 | Catino .......................... | 441/110 |
| 1,182,756 | A | * | 5/1916 | Czerkas ........................ | 441/105 |
| 1,477,627 | A | * | 12/1923 | Campbell ..................... | 441/105 |
| 1,587,605 | A | * | 6/1926 | Scroggins ...................... | 441/59 |
| 2,355,614 | A | * | 8/1944 | White ........................... | 441/110 |
| 3,859,990 | A | * | 1/1975 | Simon ........................... | 601/157 |
| 4,722,329 | A | * | 2/1988 | Kalvag .......................... | 602/32 |
| 5,078,126 | A | * | 1/1992 | Perry ............................. | 606/241 |
| 5,092,589 | A | * | 3/1992 | Packer .......................... | 482/92 |

(Continued)

FOREIGN PATENT DOCUMENTS

DE 102006008197 B3 * 8/2007
JP 07275279 A * 10/1995

(Continued)

*Primary Examiner* — Loan Thanh
*Assistant Examiner* — Victor K Hwang
(74) *Attorney, Agent, or Firm* — Cooper & Dunham LLP

(57) ABSTRACT

The present invention relates to an underwater exercise and physical therapy device for joint release and spinal adjustment wherein a tube is worn on a user's upper body and weights are worn on the user's feet in a water tank having a predetermined depth wherein his feet are spaced apart from the bottom surface thereof to carry out underwater exercise and physical therapy by using the buoyant force of the tube and the gravity of the weights, thereby enabling his joints to be released, making his muscles reformed, and further adjusting and preventing his spinal diseases.

1 Claim, 3 Drawing Sheets

U.S. PATENT DOCUMENTS

| | | | | |
|---|---|---|---|---|
| 5,105,804 A | * | 4/1992 | Van Nostrand | 606/241 |
| 5,242,380 A | * | 9/1993 | Steinbrueck | 602/32 |
| 5,244,393 A | * | 9/1993 | Perry | 434/254 |
| 5,258,018 A | * | 11/1993 | Van Nostrand | 606/241 |
| 5,409,412 A | * | 4/1995 | Colon | 441/129 |
| 6,042,602 A | * | 3/2000 | Wells | 606/241 |
| 6,827,697 B1 | * | 12/2004 | Liepman | 602/32 |

FOREIGN PATENT DOCUMENTS

| | | | |
|---|---|---|---|
| JP | 11009396 A | * | 1/1999 |
| JP | 2000270903 | | 10/2000 |
| JP | 2002177351 | | 6/2002 |
| KR | 20070013966 | | 1/2007 |

* cited by examiner

UNDERWATER EXERCISE AND PHYSICAL THERAPY DEVICE FOR JOINT RELEASE AND SPINAL ADJUSTMENT

BACKGROUND OF THE INVENTION

1. Field of the Invention

The present invention relates to an underwater exercise and physical therapy device for joint release and spinal adjustment, and more particularly, to an underwater exercise and physical therapy device for joint release and spinal adjustment wherein a tube is worn on a user's upper body and weights are worn on the user's feet in a water tank having a predetermined depth wherein his feet are spaced apart from the bottom surface thereof to carry out underwater exercise and physical therapy by using the buoyant force of the tube and the gravity of the weights, thereby enabling his joints to be released, making his muscles reformed, and further adjusting and preventing his spinal diseases.

2. Background of the Related Art

While a person is walking, generally, relatively large load is applied to his joints, and especially, if impact load is applied to him, his cartilage is injured or pressed, which eventually causes joint diseases. Further, if he is over-weighed, his joints are more injured and pressed, and in this case, if no treatment is made, his joint diseases become more severe. Thus, physical therapy is needed to release the joints and to return them to their original position.

The physical therapy is conventionally used to contract and release the muscles of a human body, improve the blood circulation and provide pain relief, by using physical energy like heat, electricity, light, hot water, cold water, motion and so on. Among the physical therapy, underwater physical therapy is most recommended for the people having joint diseases.

The underwater physical therapy is performed to remove the weight load applied to a user's knee and ankle joints by using buoyant objects in water, thereby providing effective muscle exercises, enhancing the effects of the muscle exercises, and obtaining muscle strengthening through water resistance.

SUMMARY OF THE INVENTION

Accordingly, the present invention has been made in view of the above-mentioned problems occurring in the prior art, and it is an object of the present invention to provide an underwater exercise and physical therapy device for joint release and spinal adjustment that allows a user's head to be buoyed up above the surface of water by using a buoyant force generated from a tube fitted around his upper body and at the same time allows his lower body to be pulled down below the surface of water by using the weight generated from weights worn on his feet, whereby the underwater exercise and physical therapy are carried out, thereby enabling the user's joint releasing and muscle reforming.

It is another object of the present invention to provide an underwater exercise and physical therapy device for joint release and spinal adjustment which is provided with a tube and weights connected to each other by means of elastic bands, on the basis of natural sciences wherein buoyancy and gravity have opposite properties to each other, thereby accomplishing more effective joint releasing.

To accomplish the above objects, according to the present invention, there is provided an underwater exercise and physical therapy device for joint release and spinal adjustment that performs underwater exercise and physical therapy by allowing a user put into a water tank in which a predetermined amount of water is charged to be pulled up and down above and below the surface of water, the device including: a tube adapted to be fitted around the armpits of the user's upper body to allow his head to be buoyed up above the surface of water by using a buoyant force of air filled therein; brackets mounted at the both sides of the underside of the tube and each having a fastening through-hole formed on the lower portion thereof; a tube-fixing belt adapted to be worn around the user's waist and having hooks adapted to be locked to the fastening through-holes of the brackets; weights adapted to be worn on the user's feet and each having a plurality of weight materials detachably mounted on the underside thereof to allow the user's lower body to be pulled down below the surface of water by using the gravity generated by the weight of the weight materials; and elastic bands connected to the tube-fixing belt at one ends thereof and to the weights at the other ends thereof, for elastically supporting the buoyant force of the tube and the gravity of the weights, whereby the user's joints are released and the user's spines are adjusted by using both of the buoyant force generated from the tube and the gravity generated from the weights.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, an explanation on an underwater exercise and physical therapy device for joint release and spinal adjustment according to the present invention will be in detail given with reference to the attached drawings. In the following description, a representative embodiment will be suggested to accomplish the above-mentioned technical objects of the present invention. Another embodiments made in the present invention will be replaced with the explanation on the structure of the present invention.

According to the present invention, the underwater exercise and physical therapy device for joint release and spinal adjustment is adapted to release a user's joints by using the principle that the user pushes up by the buoyant force of a tube and pulls down by the gravity of weights when he enters a water tank. The underwater exercise and physical therapy device for joint release and spinal adjustment according to the present invention includes a water tank, a tube, weights, and elastic bands connecting the tube and the weights. The tube is adapted to be fit around the user's upper body to allow the user to be buoyed up above the surface of water charged in the water tank through the buoyant force generated therefrom, and contrarily, the weights are adapted to be fit on the user's feet to allow the user to be pulled down below the surface of water through their own weight. Especially, the tube and the weights are elastically supported by means of the elastic bands. As a result, effective underwater joint releasing exercises can be carried out through the underwater exercise and physical therapy device for joint release and spinal adjustment according to the present invention.

Now, the present invention will in detail explained, but it is not limited just to the embodiment as described below.

Figure 1:
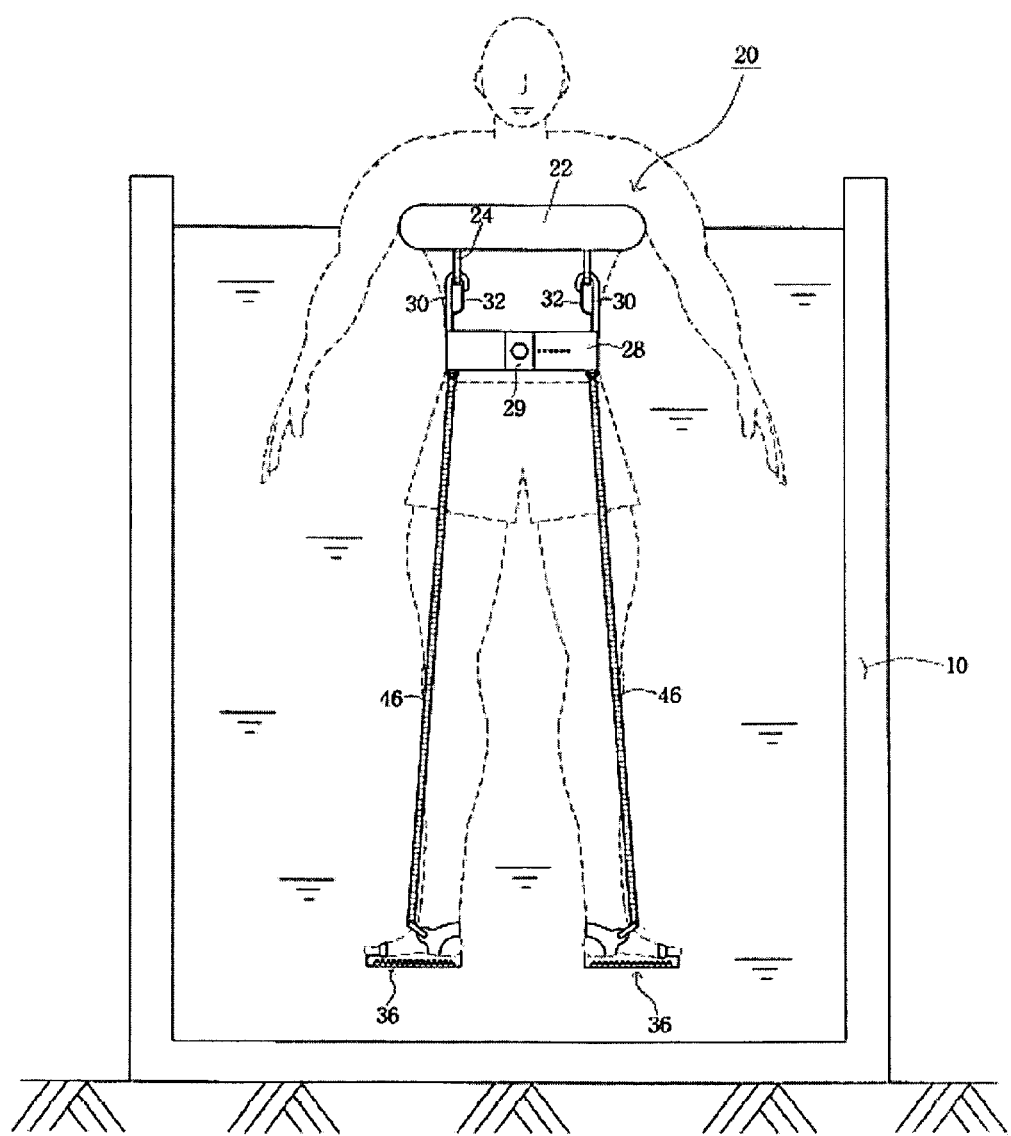
FIG. 1 is a perspective view showing a state wherein physical therapy is performed by using an underwater exercise and physical therapy device for joint release and spinal adjustment according to the present invention.
Figure 2:
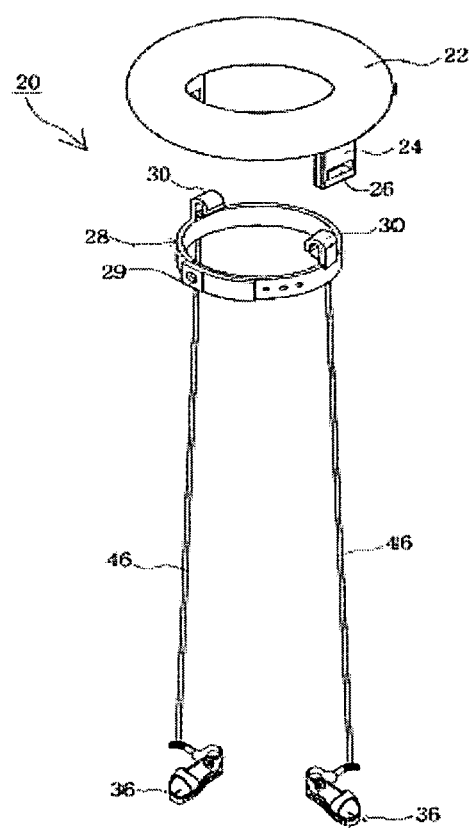
FIG. 2 is a perspective view showing the structure of the underwater exercise and physical therapy device of FIG. 1.

FIG. 1 is a perspective view showing a state wherein physical therapy is performed by using an underwater exercise and physical therapy device for joint release and spinal adjustment according to the present invention, and FIG. 2 is a perspective view showing the structure of the underwater exercise and physical therapy device for joint release and spinal adjustment of FIG. 1.

As shown in FIGS. 1 and 2, the underwater physical therapy is capable of reducing the weight load of a user's knee and ankle joints by utilizing the buoyancy of water, thereby enabling effective muscle exercises, and so as to carry out the underwater physical therapy, a water tank 10 in which a predetermined amount of water W is charged to enable the user's head to be buoyed up above the surface of water. In the water tank 10, the user who wears an underwater exercise and physical therapy device 20 for joint release and spinal adjustment according to the present invention is put and performs underwater exercising thereinto.

The underwater exercise and physical therapy device 20 for joint release and spinal adjustment according to the present invention largely includes a tube 22, a tube-fixing belt 28, weights 36, and elastic bands 46.

The tube 22 is means that floats on the surface of water by using the buoyancy of the air filled therein, and the tube 22 is locked at the user's armpits in the state of being fitted around the user's upper body, thereby allowing the user to be buoyed up above the surface of water.

Brackets 24 are mounted at the both sides of the underside of the tube 22, and each of the brackets 24 has a fastening through-hole 26 formed at the lower portion thereof. The fastening through-holes 26 of the brackets 24 are adapted to allow hooks 30 formed on the tube-fixing belt 28 to be locked thereinto.

The tube-fixing belt 28 is adapted to be worn around the user's waist to fix the tube 22 fitted around the user's upper body thereto and is also adapted to fix the tube 22 and the weights 36 thereto by means of the connection of the elastic bands 46. The tube-fixing belt 28 is formed of a strand having a predetermined length and is cut at the both end portions thereof. Fastening members 29 are provided at the both end portions of the tube-fixing belt 28, such that the both end portions of the tube-fixing belt 28 after the belt 28 is worn around the user's waist can be coupled with each other and separated from each other in accordance with the fastening and releasing of the fastening members 29.

The hooks 30 are mounted at the both sides of the top surface of the tube-fixing belt 28 and are locked to the fastening through-holes 26 formed on the brackets 24 of the tube 22, thereby allowing the tube-fixing belt 28 to be coupled to the tube 22. At this time, each of the hooks 30 has Velcro tape 32 attached thereon, and after the hooks 30 are locked to the fastening through-holes 26, the hooks 30 do not escape from the fastening through-holes 26 by means of the Velcro tape 32.

The weights 36 are adapted to be worn on the user's feet, and each of the weights 36 has a plurality of weight materials 44 detachably mounted on the underside thereof to allow the user's lower body to be pulled down below the surface of water by using the weight of the weight materials 44.

Figure 3:
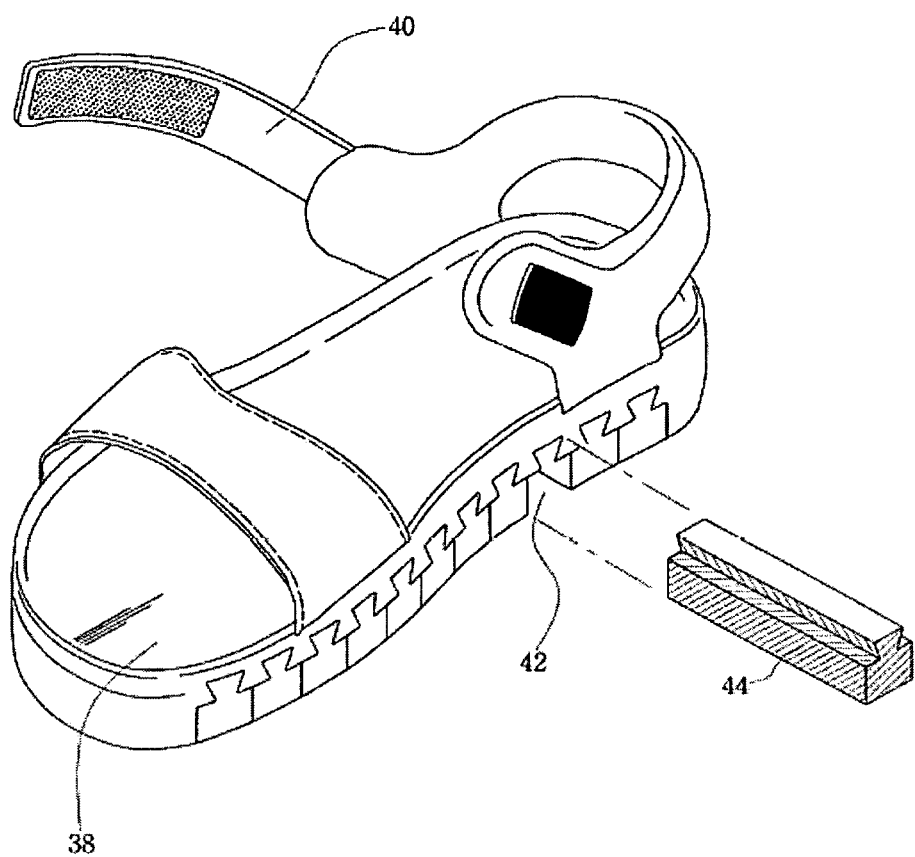
FIG. 3 is a perspective view showing the structure of the weight in the underwater exercise and physical therapy device of FIG. 2.

FIG. 3 shows the detailed structure of the weight 36.

As shown, the weight 36 has a generally footwear-like shape and includes a sole 38 having a cushion force and a plurality of insertion holes 42 formed along the underside thereof, a belt 40 mounted on the upper portion of the sole 38 for fixing the user's foot thereonto, and a plurality of weight materials 44 adapted to be detachably inserted into the plurality of insertion holes 42, for adjusting the weight of the weight 36.

Under the structure of the weight 36 as mentioned above, the weight of the weight 36 is adjusted by inserting or removing the weight materials 44 into or from the insertion holes 42 of the sole 38 in accordance with the user's joint parts or joint disease states. After that, the user's foot is placed on the sole 38 and is fixed thereonto by means of the belt 40, thereby easily completing the wearing of the weight 35.

The elastic bands 46 are adapted to elastically connect the tube 22 and the weights 36, and each of the elastic bands 46 is connected to the tube-fixing belt 28 at one end thereof and connected to the belt 40 of the weight 36 at the other end thereof, thereby elastically supporting the tube 22 buoyed up above the surface of water and the weights 36 pulled down below the surface of water.

Hereinafter, an explanation of the operation of the underwater exercise and physical therapy device for joint release and spinal adjustment according to the present invention will be given. If the user desires to carry out underwater physical therapy like his joint releasing, he first wears the weights 36 of the underwater exercise and physical therapy device 20 on his feet, and then, the tube 22 is fitted locked to his armpits. Next, the tube-fixing belt 28 is fitted around his waist and the hooks 30 mounted an the tube-fixing belt 28 are locked to the fastening through-holes 26 formed on the brackets 24 of the tube 22, thereby completing the wearing of the underwater exercise and physical therapy device 20 for joint release and spinal adjustment.

When the user wearing the underwater exercise and physical therapy device 20 for joint release and spinal adjustment enters the water tank 10, the tube 22 locked to his armpits allows him to be buoyed up above the surface of water by the buoyancy of air filled therein, and contrarily, the weights 36 worn on his feet allows him to be pulled down below the surface of water, that is, in a direction of gravity, by the weight thereof. At this time, the user's joint parts become released and physically treated by means of the buoyant force of the tube 22 and the gravity of the weights 36 working in the opposite directions to each other.

During the physical therapy, furthermore, the buoyant force of the tube 22 and the gravity of the weights 36 are supported by means of the elasticity of the elastic bands 46, thereby improving the user's exercise effects.

As set forth in the foregoing, there is provided the underwater exercise and physical therapy device for joint release and spinal adjustment that allows the user's head to be buoyed up above the surface of water by using the buoyant force generated from the tube and contrarily allows the user to be pulled down below the surface of water by using the weight generated from weights worn on his feet, such that the user's joint parts become released by means of the buoyant force of the tube and the gravity of the weights working in the opposite directions to each other and the user's muscles become reformed through the underwater exercise and physical therapy.

Additionally, the underwater exercise and physical therapy device for joint release and spinal adjustment is provided with the elastic bands elastically connecting the tube and the weights, thereby accomplishing more effective physical therapy.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An underwater exercise and physical therapy device for joint release and spinal adjustment of a user, the device comprising:
   a buoyant tube adapted to fit around a user's upper body said to comprising an underside, wherein the underside of the tube has two sides;
   brackets mounted at the sides of the underside of the tube, each bracket having a fastening through-hole formed on a lower portion thereof;
   a tube-fixing belt adapted to be worn around a user's waist, said belt having hooks adapted to be locked to the fastening through-holes of the brackets;
   weights adapted to be worn on a user's foot, each weight comprising a plurality of weight materials detachably mounted on the underside thereof; and
   elastic bands connected to the tube-fixing belt at a first end thereof and to the weights at a second end thereof, for elastically connecting the buoyant tube and the weights.

* * * * *